United States Patent [19]

Ellgass

[11] Patent Number: 5,037,393
[45] Date of Patent: Aug. 6, 1991

[54] NON-REUSABLE SYRINGE

[76] Inventor: Louis P. Ellgass, Route de Chamblioux 36, Fribourg 6, Switzerland, CH-1700

[21] Appl. No.: 378,191
[22] PCT Filed: Nov. 7, 1988
[86] PCT No.: PCT/EP88/01007
§ 371 Date: Jun. 28, 1989
§ 102(e) Date: Jun. 28, 1989
[87] PCT Pub. No.: WO89/04187
PCT Pub. Date: May 18, 1989

[51] Int. Cl.$^5$ .............................................. A61M 5/00
[52] U.S. Cl. .................................... 604/110; 604/218
[58] Field of Search ............... 604/110, 128, 181, 187, 604/218, 220-222, 229, 234

[56] References Cited

U.S. PATENT DOCUMENTS

| 4,493,703 | 1/1985 | Butterfield | 604/110 |
| 4,731,068 | 3/1988 | Hesse | 604/218 |
| 4,775,364 | 10/1988 | Alles | 604/228 |
| 4,781,684 | 11/1988 | Trenner | 604/110 |

FOREIGN PATENT DOCUMENTS 2181580 12/1973 France .
2117249 10/1983 United Kingdom .
8902287 3/1989 World Int. Prop. O. .......... 604/110

*Primary Examiner*—Stephen C. Pellegrino
*Assistant Examiner*—Michael Rafa
*Attorney, Agent, or Firm*—Griffin, Branigan & Butler

[57] ABSTRACT

A non-reusable syringe comprising a syringe body having a lower extremity closed by a base provided with a cone to receive a needle and a shaft terminated by a piston sliding tightly in the syringe body. A resilient flexible plate having a diameter greater than the inner diameter of the syringe body and thus inducing through its curvature a weak frictional force enabling the displacement of the shaft in a first direction and a strong frictional force opposing displacement of the shaft in the other direction is mounted in the shaft. To avoid attempted reuse of the syringe, a zone of weak resistance to breakage by traction is provided on the shaft. This zone break under a traction lower than the strong frictional force, but greater than the weak frictional force.

9 Claims, 13 Drawing Sheets

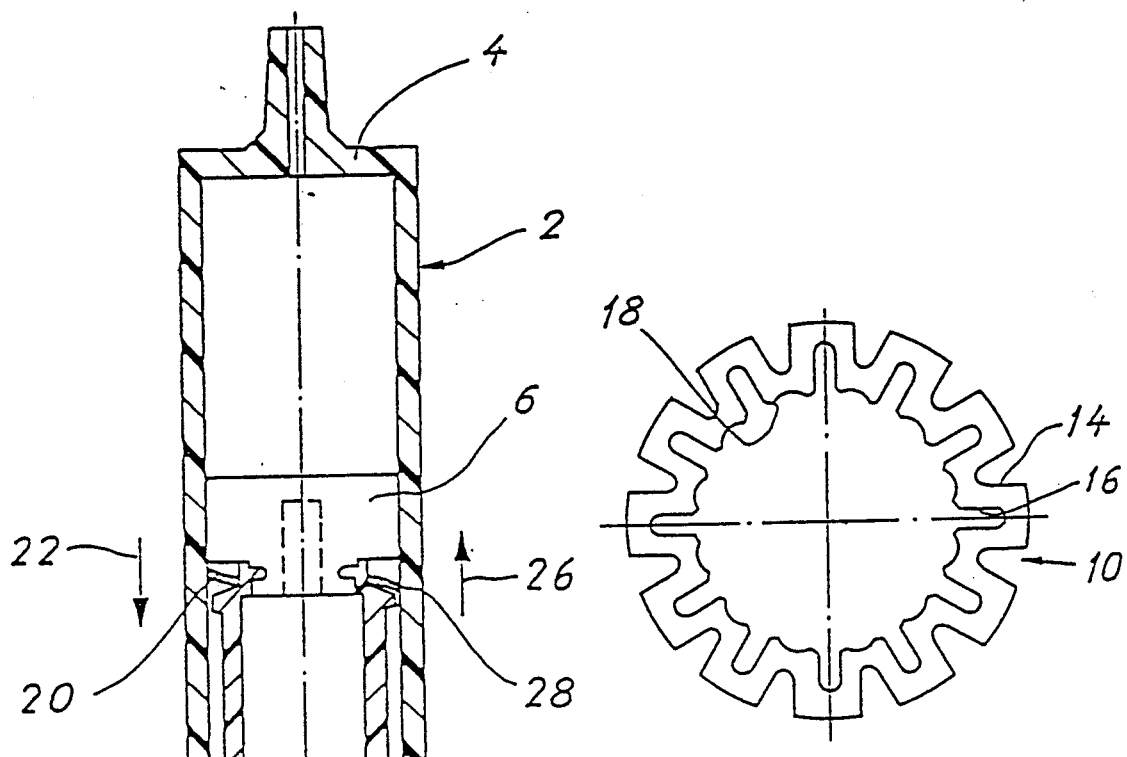
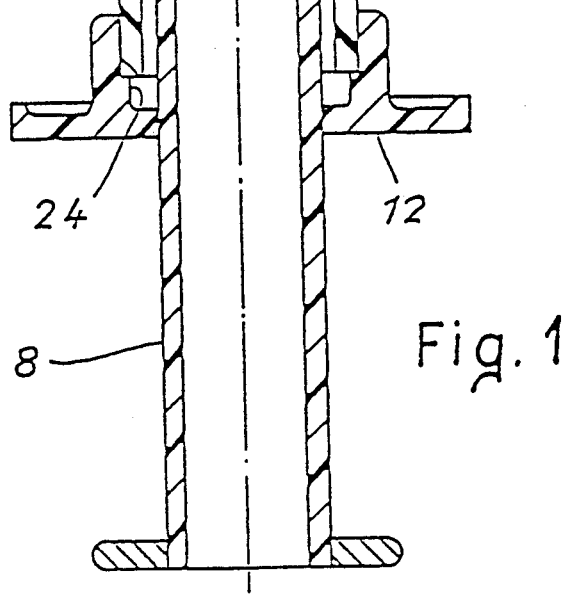
Fig. 2
Fig. 1  Prior Art drawings
FR-A-2181580

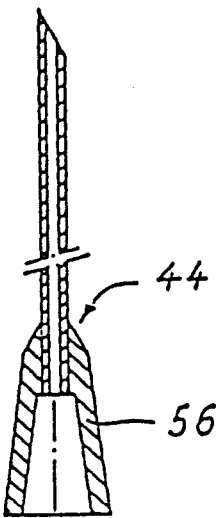
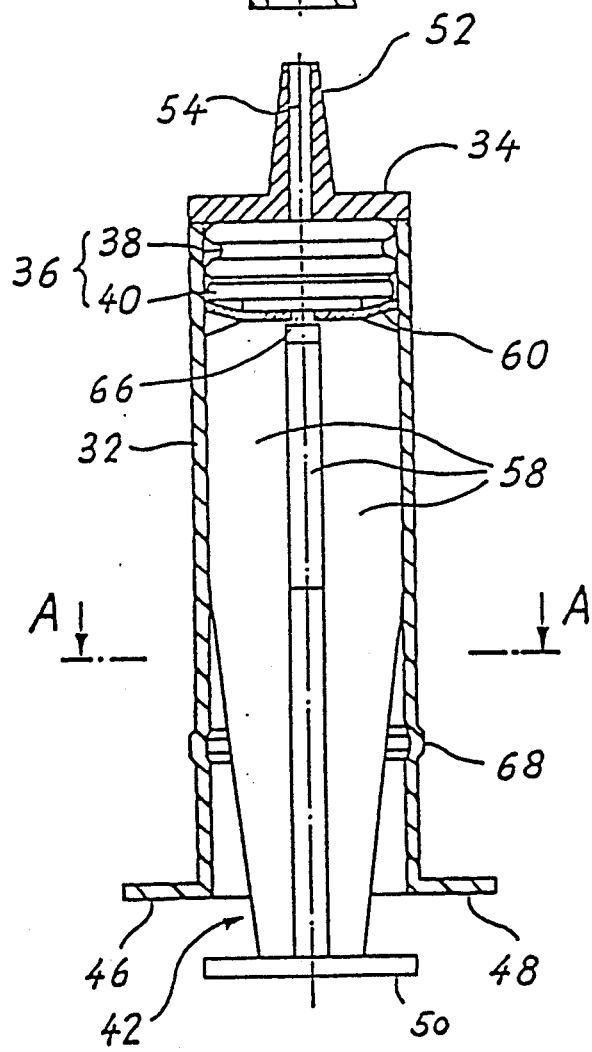
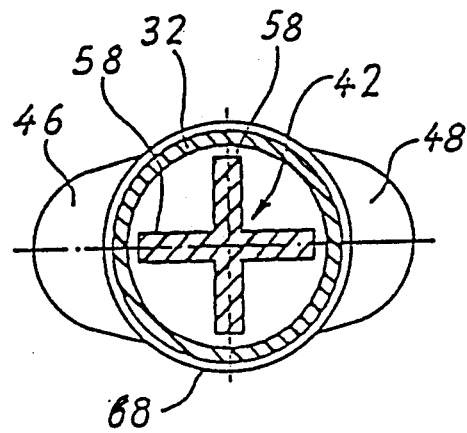
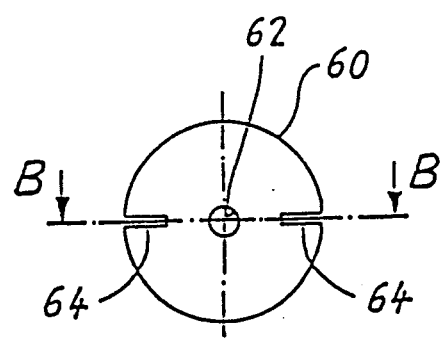
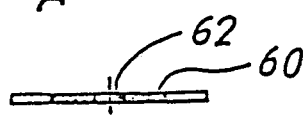

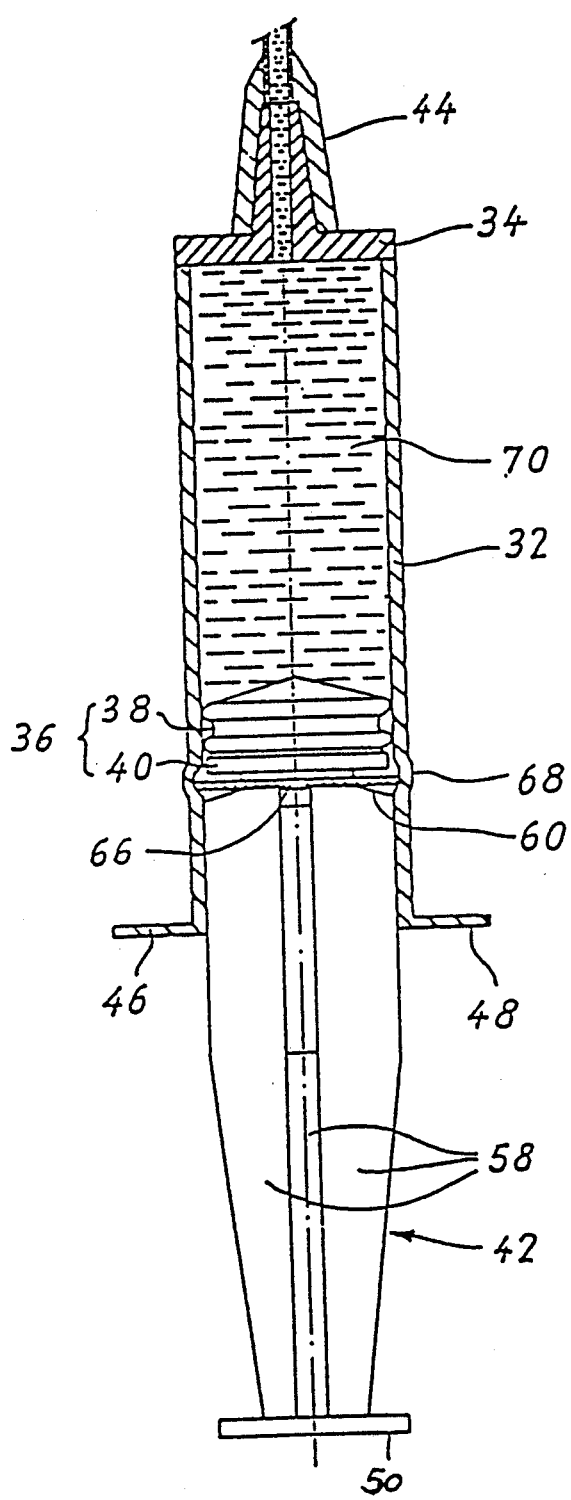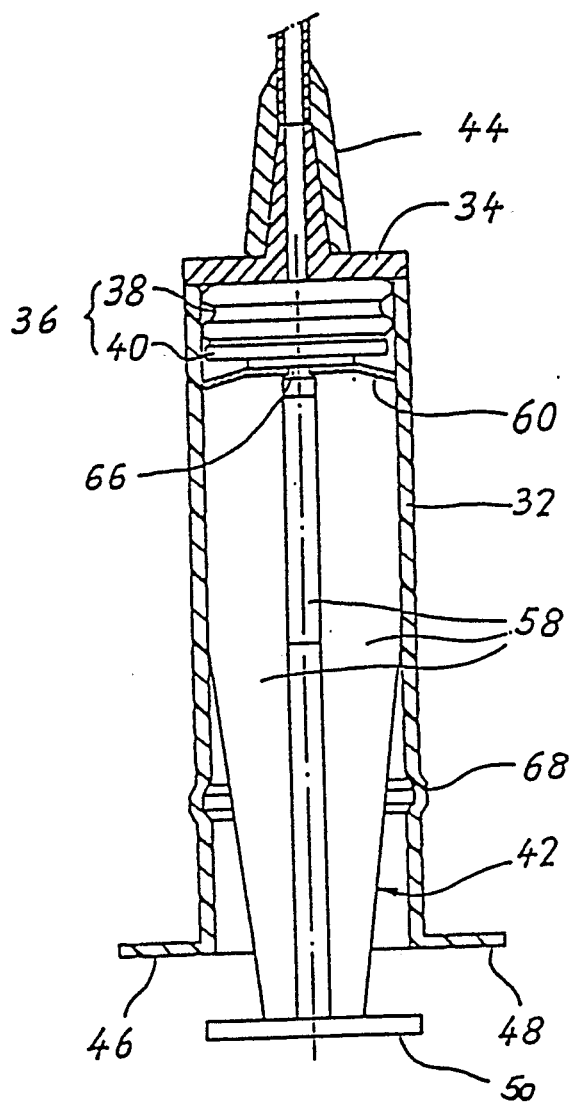
Fig. 6
Fig. 7

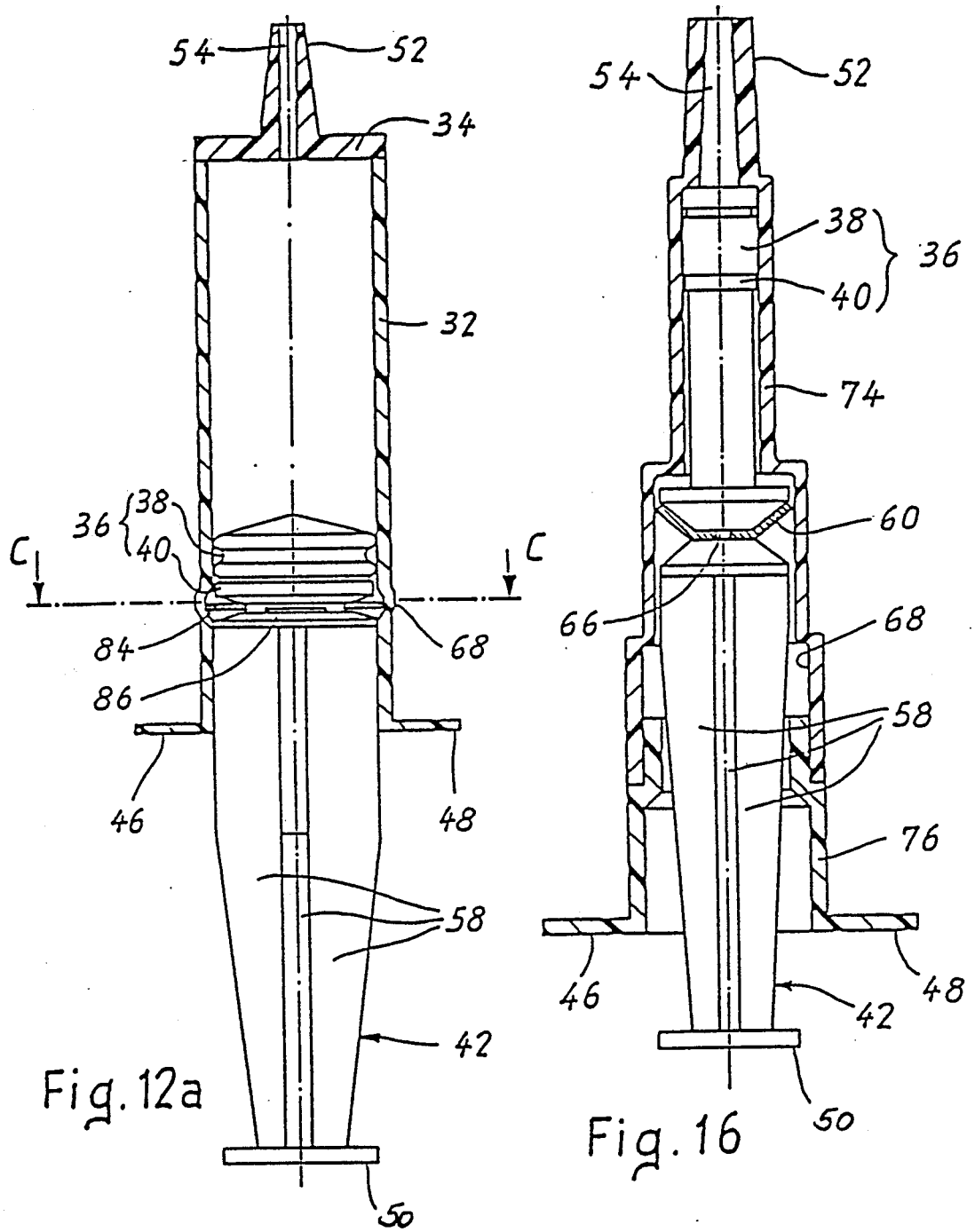
Fig. 12a
Fig. 16
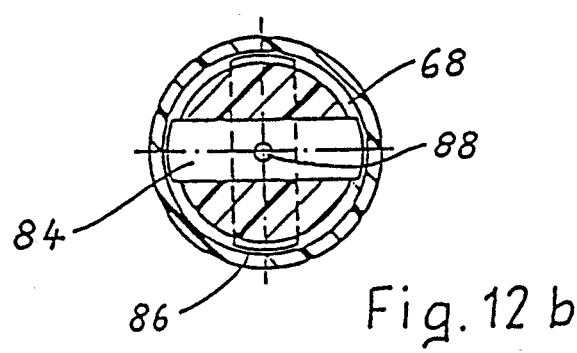
Fig. 12b

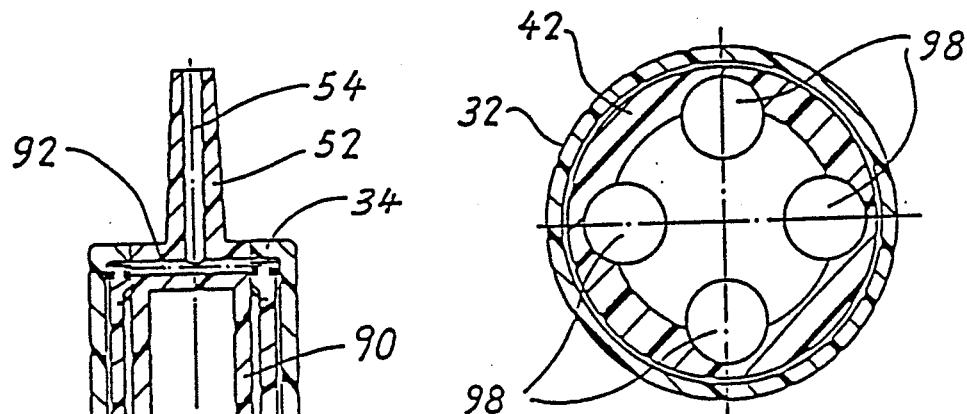
Fig. 15
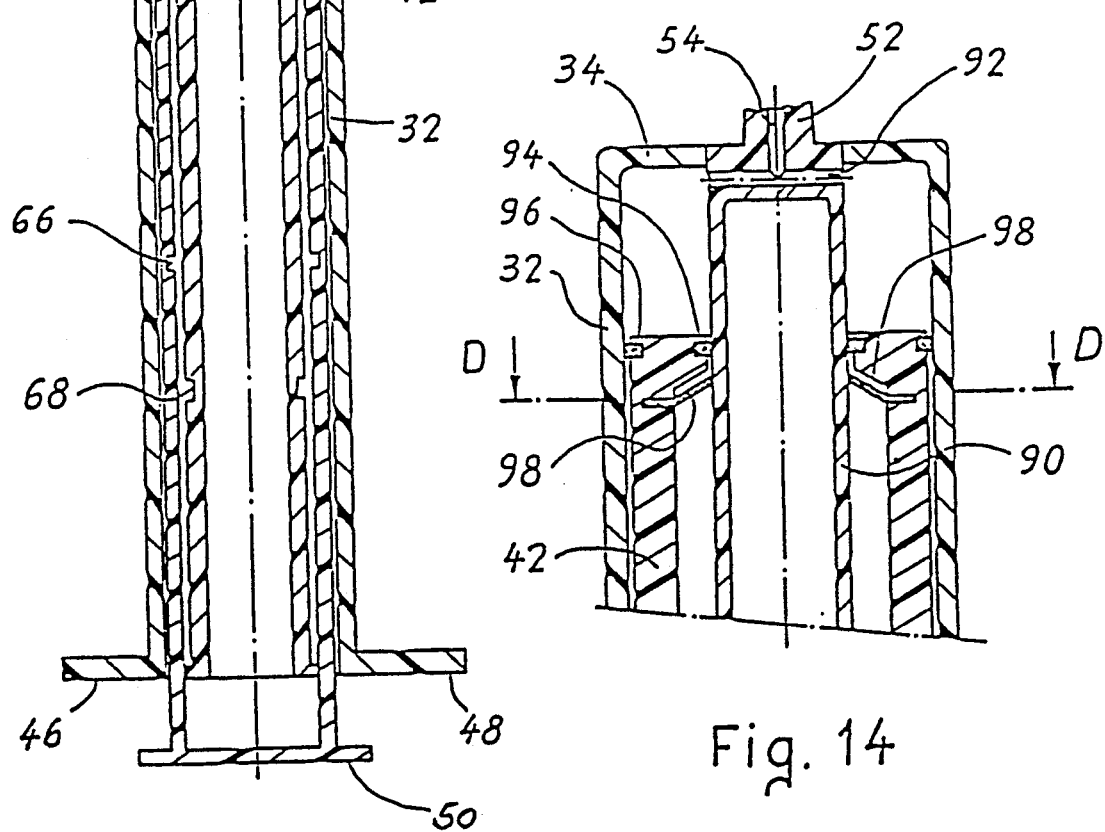
Fig. 13
Fig. 14

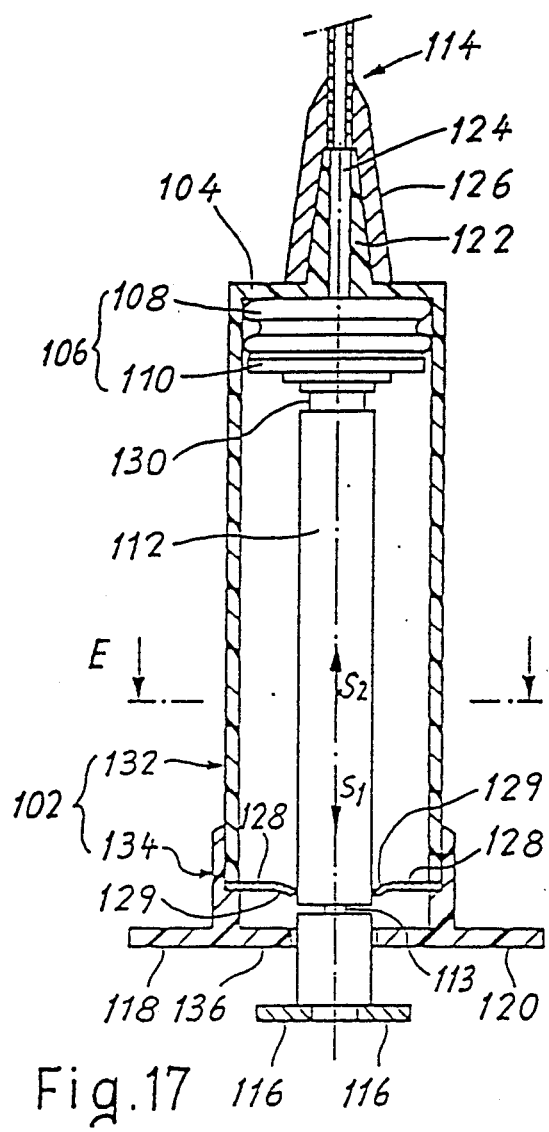
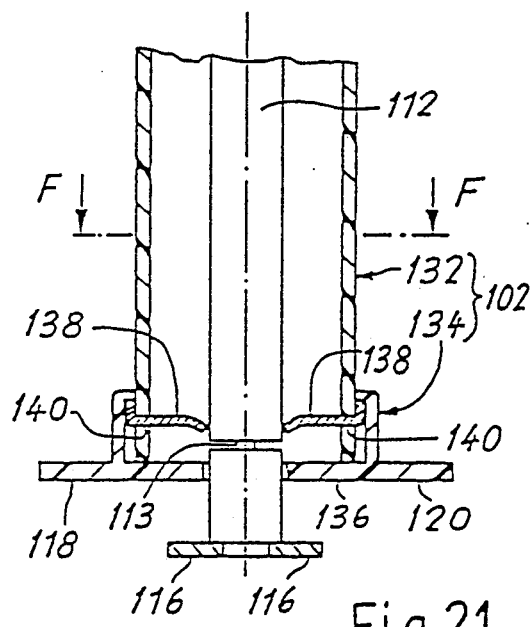
Fig. 17  Fig. 21
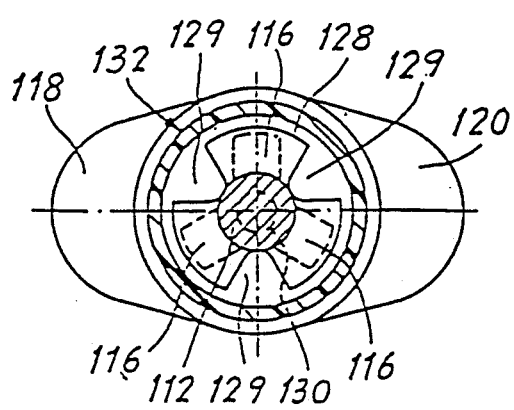
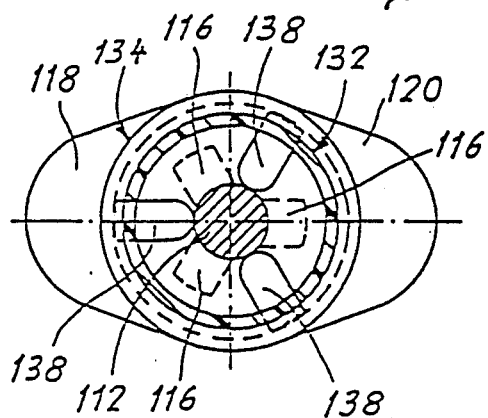
Fig. 18  Fig. 22

NON-REUSABLE SYRINGE

The present invention relates to a syringe element for an autoblocking, non-reusable syringe, that is a syringe the piston of which blocks automatically at the end of the injection and also to a syringe having an undetachable needle.

BACKGROUND OF THE INVENTION

A conventional syringe has a needle and a syringe element comprising a syringe body the lower extremity of which is provided with a base on which the needle may be fitted and a piston mounted at the end of a shaft. This piston is introduced through the upper extremity of the syringe body and is able to slide freely therewithin. In a syringe of this kind the body of the syringe and the piston can be reused.

This syringe is not satisfactory from the hygienic point of view since it introduces the risk, if used successively by several different people, of transmitting microbial germs or viruses between these people.

DESCRIPTION OF RELATED ART

Non reusable syringes are described especially in patents Nos. CH-A-478354, CH-A-620126, U.S. Pat. Nos. 469,614 and 468,467. The syringes described in these documents comprise means for destroying the piston seal or for separating the piston and the shaft, thereby preventing reuse of the syringe.

The first disadvantage of these known syringes lies in their complexity, which is reflected in their high basic cost.

A second disadvantage is the insufficient safety of these syringes. To prevent reuse of these syringes it is necessary for the piston to be pushed down to the lower extremity of the syringe body during injection. However, provided the piston is not pushed down to the base of the syringe body the syringe can be reused numerous times.

A lens complicated non-reusable syringe is described in patent No. FR-A-2181580. This syringe comprises a flexible resilient washer disposed around the shaft in the syringe body. FIGS. 1 and 2 of the accompanying drawings respectively illustrate a longitudinal section of such a syringe and a plan view of the washer.

This syringe conventionally comprises a syringe body 2 provided with a base 4, a piston 6 able to slide tightly within the syringe body and a shaft 8 for moving the piston. It also comprises a washer 10 disposed around the shaft in the proximity of the piston and a cover 12 which closes the syringe body and thereby prevents removal of the washer and the piston from the syringe body.

The washer 10 has an outer diameter greater than the inner diameter of the syringe body. It is provided with slits 14, 16 which give it a certain flexibility and make it possible to bend it in order to place it in the syringe body. It is also provided with points 18 on its inner edge in order to be able to catch onto the shaft.

The syringe is assembled with the washer in position 20 and the shaft retracted inside the syringe body. In this position the outer edge of the washer exerts a friction which only permits movement of the shaft in the direction indicated by the arrow 22. When the shaft is retracted completely the washer reaches a groove 24 in which its outer edges is no longer in contact with the syringe body. The shaft can then be pushed in the direction shown by the arrow 26 and the washer adopts the configuration shown at 28. As from this moment, it is no longer possible to displace the shaft in the direction of the arrow 22 since, if such a movement is attempted, the outer edge of the washer catches onto the wall of the syringe body and, through deformation of the washer, the points 18 penetrate into the shaft and finally shatter it.

This syringe is simpler than the syringes described in the patents cited above, but it is still nevertheless not entirely satisfactory.

Its selling price remains high because it is necessary to machine the washer carefully to produce the points 18, the role of which is essential both for causing the washer to catch onto the shaft in normal use and for shattering the shaft in the event of attempted second use of the syringe.

Moreover, the syringe is difficult to produce in practice since the washer has to possess two opposing properties: it has to be flexible to oppose only slight friction in the direction of sliding of the shaft, but it must also be sufficiently rigid so that the points penetrate into the shaft in the event of attempted second use of the syringe.

It is the object of the invention to overcome the disadvantages of known single-use syringes.

SUMMARY OF THE INVENTION

According to the present invention therefore there is provided a non-reusable syringe element comprising a syringe body having a lower extremity provided with a base pierced by a channel and an upper extremity, a tightly fitting piston slidably mounted in said syringe body to draw up or expel a product through said channel, a shaft having a lower extremity to which said piston is fixed and an upper extremity projecting beyond said upper extremity of said syringe body to displace said piston and friction means to oppose a weak frictional force on displacement of the piston in one direction and to oppose a strong frictional force on displacement of the piston in the other direction, said syringe element being characterized in that said friction means has at least one flexible resilient plate mounted on said shaft, each plate having an edge resting against the wall of said syringe body and being resiliently curved between said wall and said shaft and in that said shaft has a zone of weak resistance such that the force necessary to shatter the shaft through traction lies between said weak frictional force and said strong frictional force.

Also according to the present invention there is provided a non-reusable syringe element comprising a syringe body having a lower extremity provided with a base pierced by a channel and an upper extremity, a tightly fitting piston slidably mounted in said syringe body to draw up or expel a product through said channel, a shaft having a lower extremity to which said piston is fixed and an upper extremity projecting beyond the upper extremity of said syringe body to displace said piston and a friction means to oppose a weak frictional force on displacement of the piston in one direction and a strong frictional force on displacement of the piston in the other direction, said syringe element being characterized in that said friction means has at least one resiliently flexible plate mounted on said syringe body, each plate having an edge resting against the shaft and being resiliently curved between said wall and said shaft and in that said shaft has a zone of weak resistance such that the force necessary to shatter the shaft by traction lies between said weak frictional force and said strong frictional force.

Also according to the present invention there is provided a syringe comprising a syringe barrel having a lower extremity closed by a base and an upper open extremity, said base having a nozzle pierced by a channel; a shaft terminated by a piston slidably mounted in said syringe barrel; and a hollow needle having a base and a conduit, said base having a cavity to permit said base to fit in tight manner onto said nozzle, said channel linking said conduit to said syringe barrel, said syringe being characterized in that it comprises at least one fixing means, each fixing means being composed of a tongue on the inside face of the nozzle, each tongue comprising a cavity communicating with the channel, and an indentation on the inside face of the base, said fixing means being so disposed as to permit insertion into, and prevent subsequent extraction of the needle from, the syringe barrel and in that said syringe comprises means for linking each indentation to the outside of the syringe.

BRIEF DESCRIPTION OF THE DRAWINGS

These characteristics and the advantages of the invention emerge more clearly from the following description, given for the purposes of illustration, but which are not limiting, with reference to the appended drawings in which:

FIG. 1 and 2, already described, illustrate respectively a longitudinal section of a non-reusable prior art syringe and a plan view of a washer forming part of said syringe.

FIG. 3a is a longitudinal section illustrating a syringe element according to a first embodiment of the invention, FIG. 3b is a longitudinal section illustrating a needle adapted to fit on the syringe element of FIG. 3a to form a single-use needle, FIG. 4 is a transverse section along the axis AA of FIG. 3a, FIG. 5a is a plan view of a washer for mounting on the syringe body, FIG. 5b is a section along the axis BB of the washer shown in FIG. 5a, FIG. 6 is a longitudinal section illustrating the positions of the piston and of the washer of the syringe shown in FIGS. 3a and 3b, after the aspiration or drawing up phase, FIG. 7 is a longitudinal section illustrating the positions of the piston and of the washer of the syringe of FIG. 3a and 3b after the injection or expulsion phase, FIG. 12a illustrates a longitudinal section of a syringe of the invention and FIG. 12b a transverse section along the axis CC of FIG. 12a, these figures showing a friction means composed of two slides, FIG. 13 is a longitudinal section illustrating a syringe element according to the invention for a small volume syringe, FIG. 14 is an enlarged view of the lower part of the syringe element shown in FIG. 13, FIG. 15 is a transverse section along the axis DD of FIG. 14, FIG. 16 is a longitudinal section illustrating another syringe element according to the invention for a small volume syringe, FIG. 17 is a longitudinal section illustrating a syringe element according to a second form of execution of the invention, FIG. 18 is a transverse section along the axis EE of FIG. 17, FIGS. 19 and 20 show the positions of the piston and of the washer after the drawing up phase and after the injection phase respectively of a syringe having a syringe element as shown in FIG. 17, FIG. 21 is a longitudinal section illustrating an embodiment of the syringe body of the syringe shown in FIG. 17, FIG. 22 is a transverse section along the axis FF of FIG. 21.

DESCRIPTION OF PREFERRED EMBODIMENTS

Figure 8:
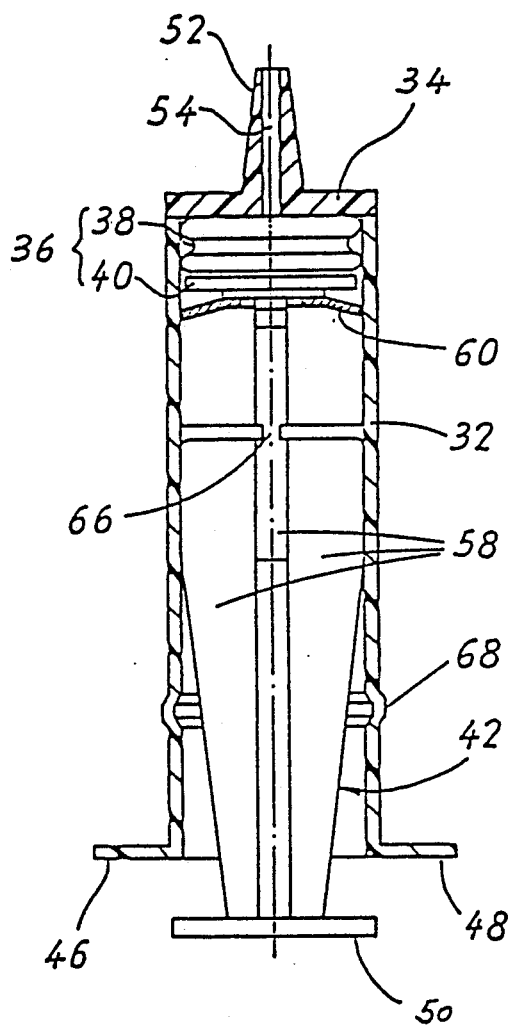
FIG. 8 is a longitudinal section illustrating an embodiment of the syringe element shown in FIG. 3a in which the zone of weak resistance of the shaft is situated between the washer and the upper extremity of the shaft.

In the following description there are considered for purposes of example syringe elements the syringe body of which is cylindrical. The piston then possesses axial symmetry and generally presents the form of a disc in transverse section. In can also present an annular form in transverse section (see FIG. 13).

It should nevertheless be clearly understood that the invention is not limited to syringe elements having a cylindrical syringe body, but also applies regardless of the section of the body of the syringe. In particular, syringe elements having an ellipsoid, square or rectangular syringe body, fall within the scope of the invention.

There are shown in longitudinal section in FIGS. 3a and 3b respectively a syringe element in accordance with the invention and a needle adapted to be fitted to this syringe element, the whole forming a single-use syringe.

This syringe conventionally comprises a syringe body 32 of generally cylindrical shape, a base 34 fixed to a first extremity, termed lower extremity, of the syringe body, a piston 36 having a resilient element 38 fixed onto a rigid support 40, a shaft 42 integral with the piston and a hollow needle 44 adapted to be fixed to the base 34. Support surfaces 46, 48 and 50 are also provided on the free extremity of the shaft and in the vicinity of the second extremity, termed upper extremity, of the syringe body to simplify handling of the piston. The syringe body between the lower extremity and the upper extremity is commonly referred to as the barrel. The base 34 of the syringe body has a cone 52, pierced by a channel 54, designed to receive the needle 44. This latter comprises a conical hollow base 56 which fits closely onto the cone 52. The shaft 42 comprises wings 58 which ensure its correct guidance in the syringe body. The shaft is cruciform in cross section as shown in the transverse section represented in FIG. 4.

According to the invention the syringe element also comprises a friction means and the shaft comprises a zone presenting a weak resistance to breakage.

In the embodiment shown in FIG. 3a the friction means is composed of a flexible resilient washer 60, shown in FIGS. 5a and 5b. This washer is provided with an orifice 62 for passage of the shaft and slits 64 which give it a certain flexibility.

It will be noted that the shaft 42 collars on both sides of the washer 60 that are wider than the diameter of the orifice 62 of the washer thereby rendering this integral with the shaft. In practice, the fitting of the washer onto the shaft can be effected simply by producing the shaft by plastic injection in a mold containing the washer.

In further embodiments of the invention the friction means may be moulded integrally with the shaft and hence fabricated of the same plastics material. Such a construction has the advantage of reducing the number of manufacturing steps and rendering the syringe element cheaper.

The diameter of the washer is slightly greater than the inner diameter of the syringe body 32 and thus adopts a dished shape when it is put into place therein.

The relationship between the diameters of the washer and the syringe body depend on the materials used. For example, in the case of a syringe body in a hard plastic, such as acrylic, polyurethane, polycarbonate or polyether, having an inner diameter of 9.7 mm, it is possible to use a tempered steel spring washer of 0.1 mm thickness having a diameter of 10.3 mm.

For a syringe body of the same diameter, but produced in a soft plastic such as, for example, polyethylene or polypropylene, which tends to become deformed, it is advantageous to provide a slightly larger washer, for example of 10.6 mm diameter.

The washer presents a weak frictional force when the shaft is displaced in the direction tending to increase its curvature, but a storing frictional force when the shaft is displaced in the direction tending to decrease the curvature.

In the first example mentioned above (syringe body in hard plastic) theses forces, or more precisely the forces to be exerted to overcome the frictional forces, are of about 0.5 kg and 5 kgs respectively. In the second example (syringe body in soft plastic), they are 0.4 kg and 4 kg respectively. The weaker frictional forces in the second example are explained by the deformation of the syringe body.

The part of the shaft which traverses the washer 60 can constitute the zone 66 of weak resistance with which the shaft according to the invention is provided. This zone 66 of weak resistance can also be situated at any other point of the shaft between the washer and the support surface 44, as shown in FIG. 8. The easiest way of producing this zone of weak resistance consists in reducing the cross section of the shaft.

The resistance to breakage exhibited by this zone is selected so that it lies between the weak frictional force and the strong frictional force. In the two above examples, a resistance to breakage of about 1 to 2 kgs is defined, where the cross section of weakened shaft portion is about 1.5 mm. In the case of FIG. 3a, this cross section is defined directly by the diameter of the orifice 62 of the washer.

It will be noticed in FIG. 3a that the base 34 is fitted onto the syringe body 32. This embodiment makes it possible to place the shaft in the syringe body by introducing the washer through the lower part of the syringe body, this having the advantage of curving the washer automatically. The base is then fixed by bonding.

It is nevertheless also possible to effect a monobloc moulding of the syringe body 32 and the base 34. In this case, the washer is introduced with the shaft through the upper extremity of the syringe body 32. This calls for a special tool for curving the washer to prevent it from catching onto the wall of the syringe body during its positioning.

It will also be noted in FIG. 3a that the syringe body 32 has a groove 68 on its inner wall. This is designed to make it possible to invert the direction of curvature of the washer 60 and, for this purpose, has a diameter greater than that of the uncurved washer.

This groove, or an equivalent means, is necessary for syringes which are delivered in the position shown in FIG. 3a since it is necessary to be able to invert the direction of curvature of the washer between the drawing up phase and the injection phase.

Figure 10:
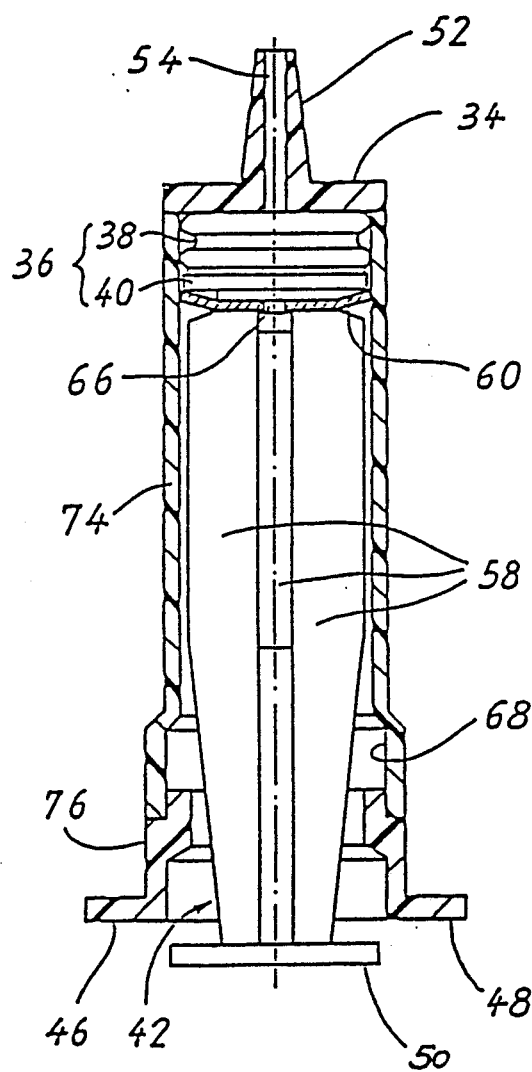
FIG. 10 is a longitudinal section illustrating another embodiment of the syringe element shown in FIG. 3a, having different arresting means.

This groove can have a width (dimension measured according to the axis of the syringe body) just sufficient to receive the washer as shown in FIG. 3a or, on the contrary, a very great width such as is shown, for example, in FIG. 10.

On the hand, this groove is not needed in prefilled syringes since their use only comprises the injection phase. In a syringe of this type the piston, prior to use, in the proximity of the upper extremity of the syringe body and the washer is curved with its concavity facing towards the support surface 44 of the shaft.

The functioning of the syringe shown in FIGS. 3a and 3b is illustrated in FIGS. 6 and 7.

The first stage consists in drawing up the product 70 to be injected by sliding the piston 36 towards the upper extremity of the syringe body. When the washer 60 reaches the groove 68 it adopts a planar form, as shown in FIG. 6. In this position it is possible to pull the shaft outside the syringe body or, on the contrary, to push it back towards the inside of the syringe body.

It is desirable, at least for syringes sold to the public, if the shaft cannot be completely extracted from the syringe body since otherwise the user could withdraw the washer and use the same syringe several times. It will be understood that this is not satisfactory from the hygienic point of view, particularly if the use is a drug addict or is infected by a virus.

Figure 9:
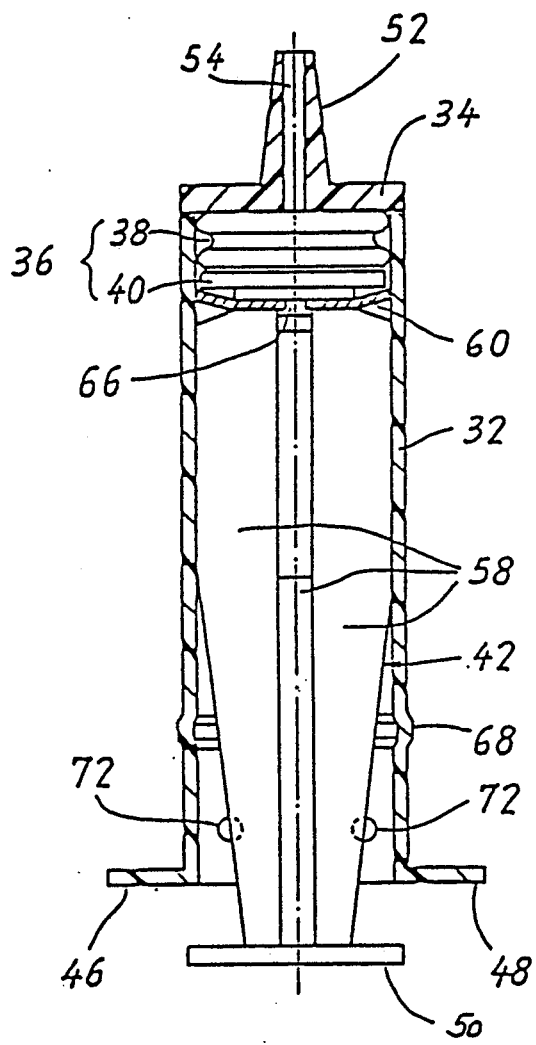
FIG. 9 is a longitudinal section illustrating an embodiment of the syringe element shown in FIG. 3a having arresting means to prevent the washer emerging from the syringe body.

A simple method for preventing the shaft from being completely extracted from the syringe body consists in molding spurs 72 onto the inner wall of the upper part of the syringe body, as shown in FIG. 9, which then form a stop for the washer 60.

One embodiment is shown in FIG. 10 with a syringe body comprising a lower part 74 and an upper part 76 fitted one into the other. The lower part 74 has an inner diameter equal to that of the piston 36. It is bounded at one extremity by the base 34 and at the other extremity by an flare having an inner diameter at least equal to the diameter of the washer 60. The upper part 76 fits into this other extremity to form a groove 68 starting from the flare of the lower part and to constitute a stop making it impossible to withdraw the washer from the syringe body.

In the case of syringes designed to be used by medical personnel one need not provide a stop for the washer 60 because such personnel is aware of the dangers of reusing a syringe.

The second stage in the functioning of the syringe consists in injecting the product 70 by pushing the piston 36 towards the base 34 of the syringe body. As soon as the washer has left the groove 68 it curves in the direction shown in FIG. 7 and, from then on, the shaft can only slide in the direction in which the shaft is being pushed inside the syringe body. FIG. 7 corresponds to the end of the injection phase; in this position the piston is blocked and the syringe cannot be reused.

In the case of the syringe shown in FIG. 10, the washer comes to a stop against the part 76 at the end of the drawing up phase. The large width of the groove 68 then makes it possible to expel the air contained in the syringe by pushing the washer towards the other edge of the groove and then to draw up a drop of blood by pulling the washer towards the part 76 again. The product is then injected normally by pushing the piston down completely in the syringe body. This double movement of the washer in the groove makes it possible, by drawing up a drop of blood, to ensure that the needle is correctly introduced into a blood vessel.

With reference to FIG. 3a a description has been given of an embodiment of a syringe element according to the invention and mention had been made of embodiments derived from the position of the zone of weak resistance of the shaft (FIG. 8) and from the stops for preventing the washer from being withdrawn from the syringe body (FIGS. 9 and 10). Other embodiments are also possible, notably in connection with the washer and the syringe body.

The washer shown in FIG. 5a has two radial slits 64 which give it the necessary flexibility, but it is clear that the same result can be obtained with slits of different shape and different number.

Figure 11A:
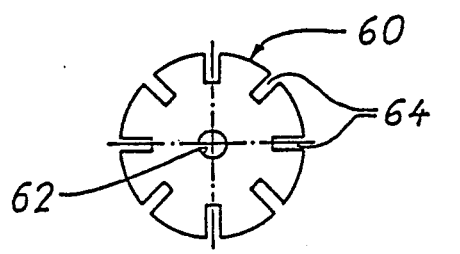
FIGS. 11a to 11d illustrate embodiments of the washer in plan view.
Figure 11B:
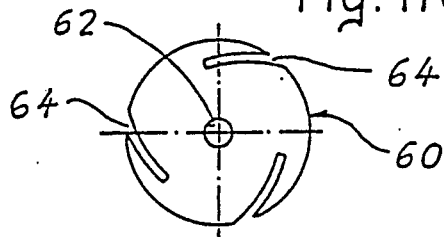
Figure 11C:
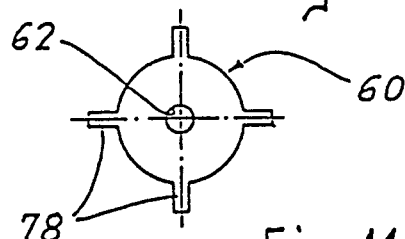
Figure 11D:
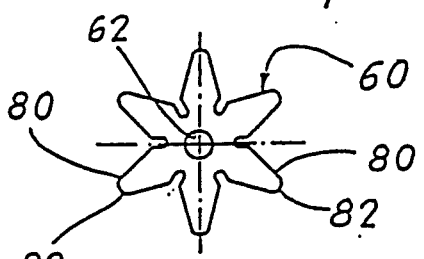

Some examples hereof are given in FIGS. 11a to 11d. In FIG. 11a, the slits 64 are radial and in relatively large number; in FIG. 11b, the slits 64 are produced in spiral form; in FIG. 11c, the slits form large recesses which only leave fine tongues 78; finally, FIG. 11d illustrates a washer having radial fingers 80, each edge 82 of which has a geometry so determined that the entire edge is in contact with the syringe body when the washer is in place, this facilitating a better sliding of the shaft in the syringe body.

Even in cases where the syringe body is cylindrical, the friction means is not necessarily a washer. It can be composed of one or several flexible and resilient plates as shown in FIGS. 12a, and 12b. These plates 84, 86 are arranged in the perpendicular plane to the axis of the shaft and have a length slightly greater than the diameter of the syringe body.

This variant is interesting since the fitting of the plates 84, 86 on the shaft 42 can be simply effected by introducing the plates in the slits provided in the shaft. It is, of course, also possible to proceed as in the case of a washer, that is to place the plates in the mold used to produce the shaft by plastic injection. In this case, it is possible to provide each plate with an orifice 88 to make each plate integral with the shaft.

The syringe element shown in FIG. 3a has a cylindrically shaped syringe body. This form is conventional for the injection of volumes of liquid greater than 5 ml. For smaller volumes, this cylindrical form leads to a small dimension syringe which is inconvenient to handle.

One embodiment of a syringe element according to the invention for the injection of small volumes of liquid is shown in longitudinal section in FIG. 13. FIGS. 14 and 15 respectively illustrate an enlarged longitudinal section of the lower part of this syringe element and FIG. 15 is a transverse section at the level of the resilient and flexible washers.

The syringe element comprises a conventional cylindrical syringe body 32, the lower extremity of which is terminated by a base 34 having a cone 52 pierced by a channel 54 and the upper extremity of which has two support surfaces 46, 48. It also comprises a cylinder 90 in the syringe body. This cylinder 90 is fixed to the base 34 and defines an annular shaped reservoir in the syringe body. A channel 92 is provided at the base of the cylinder 90 to connect this reservoir to the channel 54.

The shaft 42 has a general cylindrical shape. It is provided with two circular gaskets 94, 96 at its lower end which are placed respectively between the inner wall of the syringe body 32 and the outer wall of the shaft and between the outer wall of the cylinder 90 and the inner wall of the shaft. It also has at its upper extremity a support surface 44.

This syringe element has, in accordance with the invention, a friction means and a zone of weak resistance on the shaft. The friction means is composed of four resiliently flexible discs 98, a part of which is driven into the inner wall of the shaft and the other part of which rests resiliently on the cylinder 90.

In the position shown in FIG. 14, the washers 98 make it possible to pull the shaft outside the syringe body. In order to be able then to push the shaft towards the base of the syringe body it is necessary to invert the direction of curvature of the discs; this is possible when the discs reach the groove 68 (FIG. 13) effected in the outer wall of the cylinder 90.

In addition, the zone of weak resistance of the shaft can be simply realized by a groove 66 which reduces the thickness of the wall of the shaft.

Another embodiment of a syringe element for the injection of small volumes of liquid is shown in FIG. 16. This syringe element comprises a syringe body composed of two parts 74, 76 fitted into one another, as has already been described with reference to FIG. 10.

However, in FIG. 16, the lower part 74 does not have an identical diameter along its entire length, but on the other hand comprises a first region of small diameter and a second region of greater diameter.

As can be seen in the figure, the piston 36 always remains in the first region of the lower part 74 whilst the washer 60, mounted on the shaft 42, always remains in the second region of the lower part 74. There is thus provided a syringe for the injection of small volumes of liquid, the friction means of which remains effective since the diameter of the washer is large and which is easy for the user to handle thanks to the large diameter of the second region of the lower part 74.

For purposes of example, for a syringe of 1 ml, the syringe element can comprise a first region 19 mm in length with an inner diameter of 4.7 mm, a second region of inner diameter 9.5 mm and a groove 68 of inner diameter 11.2 mm. If the body of the syringe is produced in hard plastic, such as acrylic, polyurethane, polycarbonate or polyether, it is possible to employ a tempered steel spring washer of 0.1 mm thickness, 10.5 mm diameter and having an orifice of 1.2 mm. The diameter of this orifice determines the diameter of the shaft and, consequently, the resistance to breakage of the shaft.

There have hitherto been described various embodiments of the invention in which the friction means is mounted on the shaft and rests resiliently against the wall of the syringe body. However, the invention can also be implemented by fixing the friction means to the syringe body and by having this press resiliently against the shaft.

In further embodiments of the invention the friction means may be moulded integrally with the syringe body and hence fabricated of the same plastics material. Such a construction has the advantage of reducing the number of manufacturing steps and rendering the syringe element cheaper.

There is shown in longitudinal section form in FIG. 17 a syringe according to this embodiment. This syringe conventionally comprises a syringe body 102, a base 104 fixed to a first extremity, termed lower extremity, of the syringe body, a piston 106 having a resilient element 108 fixed on a rigid support 110, a shaft 112 to one extremity of which the piston is fixed and a hollow needle 114 adaptable on the base 104. To simplify handling of the piston there is also provided a support surface 116 on the free extremity of the shaft and support surfaces 118, 120 near the second extremity, termed upper extremity, of the syringe body.

The base 104 of the syringe body has a cone 122 pierced by a channel 124 designed to receive the needle 114. This comprises a conical hollow base 126 which fits closely onto the cone 122.

The friction means is composed of a resiliently flexible washer 128 and the zone 113 of weak resistance to breakage on the shaft is produced by a reduction in the cross section of the shaft.

The washer comprises an outer edge sealed in the wall of the syringe body 102 and an inner edge resting resiliently against the shaft 112. As shown in FIG. 17, the profile of the washer 128 between the outer edge and the inner edge is not planar, but curved.

When the washer is placed in position during manufacture of the syringe, the washer is oriented with its concavity turned towards the upper extremity of the syringe body, as shown in the figure. Through its inner edges impelled resiliently against the shaft, the washer creates a frictional force which opposes movement of the shaft in the direction S1, but permits sliding of the shaft in the direction S2.

The shape of the washer 128 is visible in FIG. 18. This washer has fingers 129 oriented in radial manner in relation to the syringe, a part of which rests resiliently against the shaft 112.

The washer 128 is fixed by its outer edge to the syringe body 102. A simple manner of producing this fixing consists in interposing the washer 128 between two parts 132, 134 which are then reunited to form the syringe body.

In this case the syringe can be manufactured in the following manner. In the first stage the lower part 132 comprising a cylindrical element and the base 104 is mounted. The piston 106 and the shaft 112 are then put into place, the piston 106 being pushed to the base 104. In a subsequent stage the washer 128 is put into position. As shown in FIG. 18, this washer has recesses for the passage of the support surfaces 116 of the extremity of the shaft 112. It is thus possible to place the washer 128 in position by simply making it slide along the shaft 112.

In this way the washer 128 curves resiliently in the desired direction.

The last stage consists in fitting the part 134 of the syringe body 102 on the part 132, these two parts being joined by bonding or other means. The outer edge of the washer 128 is thus held between the two parts 132 and 134.

The part 134 has a cylindrical element fitting on the cylindrical element of the part 132, the support surfaces 118, 120 and a cover plate 136 closing the upper extremity of the syringe body 102. This cover plate 136 comprises, as does the washer 128, recesses corresponding to the support surfaces 116. This cover plate 136 makes it possible to prevent the user reaching the washer 128.

It may be seen that the syringe of the invention can be manufactured simply and thus at little extra cost as compared to a conventional reusable syringe.

The working of the syringe of the invention will now be described with reference to FIGS. 17, 19, 20. At the beginning the syringe appears as illustrated in FIG. 17. The fingers 129 of the washer 128 have their convexity turned towards the base 104 and the piston 106 is near the base 104. In this position the shaft 112 can only be displaced in the direction S1.

This displacement corresponds to the drawing up in the syringe body of liquid 135 for injection. The shaft is displaced in this direction until the washer 128 is at the level of a groove 130 provided in the shaft 112 as shown in FIG. 19. When one then begins to push the piston 106 down towards the base 104, the inner edge of the washer 128 emerges from the groove 130 and rests resiliently against the shaft 112, the profile of the washer 128 being curved and having its concavity turned towards the base 104. In this position the shaft 112 can no longer be displaced in the direction S1, but can only slide in the direction S2.

At the end of the injection the piston 106 is near the base 104. The syringe is then unusable because the shaft 112 can neither be displaced in the direction S1 nor in the direction S2 (see FIG. 20). If, however, an attempt is made to use the syringe a second time, the shaft 112 breaks at the height of the zone of weak resistance thereby rendering any further use of the syringe totally impossible.

The syringe described with reference to FIGS. 17 to 20 is supplied to the user in the position shown in FIG. 17. This syringe therefore necessarily has a groove 130 in the shaft 112, or an equivalent means, to permit the direction of curvature of the washer to be inverted between the drawing up phase and the injection phase. This groove can have a considerable width as in the syringes shown in FIGS. 10 and 16, to permit the drawing up of a drop of blood between the phases of drawing up and injecting the product to be injected and for ensuring thereby that the needle is indeed introduced into a blood vessel.

Figures 19, 20:
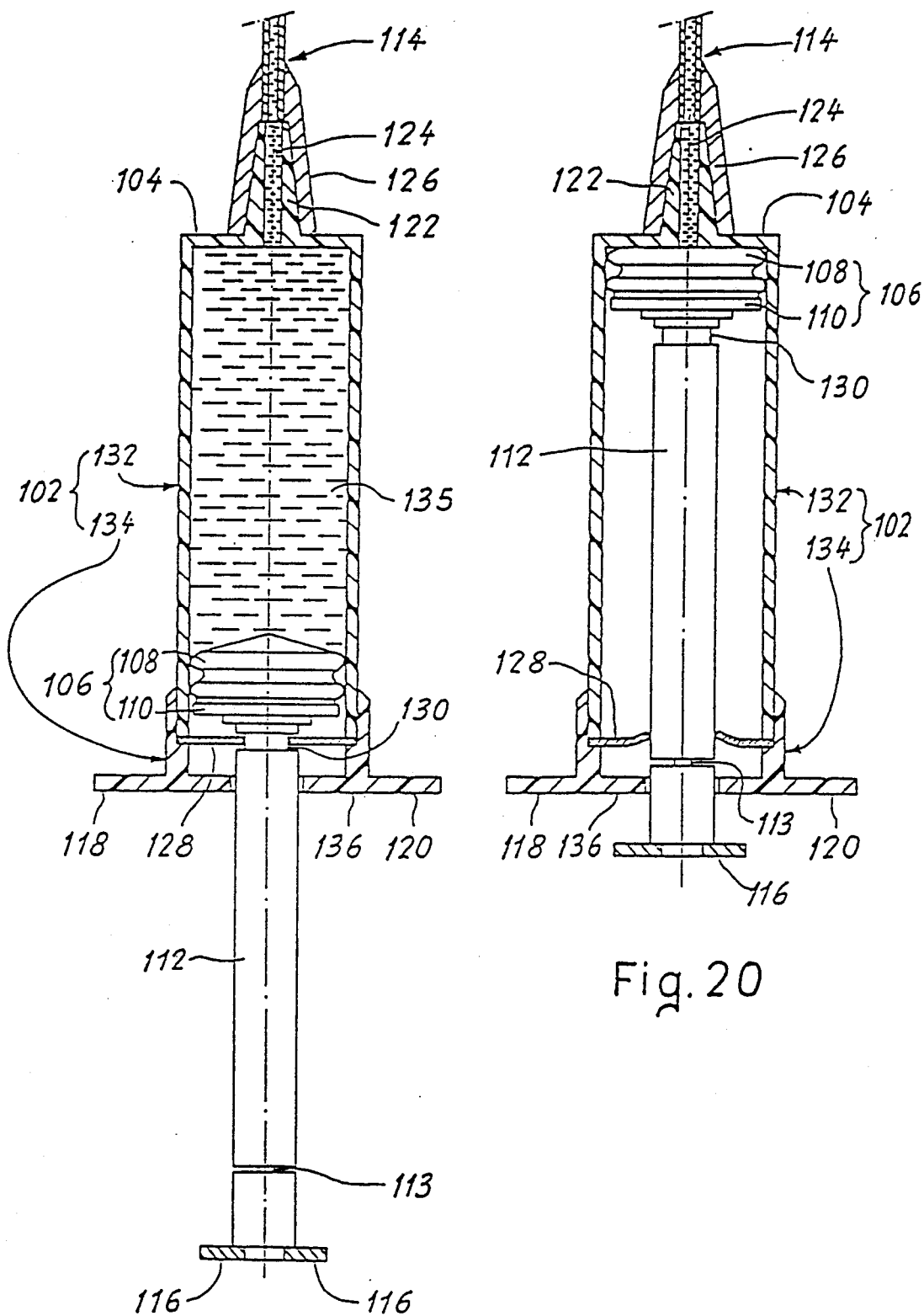

In the case of a prefilled syringe, which is therefore delivered to the user in the position shown in FIG. 19, it may be conceived that this groove 130 is not necessary if the washer is already curved in the direction permitting the injection, i.e. in the direction shown in FIG. 20.

An embodiment of the friction means and the fixing of this friction means is shown in FIGS. 21 and 22 which illustrate respectively a longitudinal section of the upper half of a syringe element and a transverse section of this syringe element. On these figures, the identical elements to those shown in FIGS. 17 to 20 have the same references.

The friction means comprise flexible and resilient slides spread regularly around the shaft 112 and radially disposed in relation thereto. These slides 138 are placed in position in the slits 140 prepared in the wall of the part 132 of the syringe body 102. The inner edge of each slide rests resiliently against the shaft 112 whereas the outer edge, which is bent back abuts against the outer face of the syringe body.

The upper part 134 of the syringe body 102 has, as in FIG. 17, a cover plate 136 closing the upper extremity of the syringe body and two support surfaces 118 and 120. It also has a cylindrical element fitting on the cylindrical element of the lower part 132. The extremity of this cylindrical element has a shape designed to attach itself to the outer edge of the slides 138.

The assembly of this syringe is substantially identical to that of the syringe shown in FIG. 17. After the putting into place of the shaft 112 and of the piston in the syringe body 102, the slides 138 are introduced in the slits 140, ensuring that the slides 138 are curved in the correct direction as shown in FIG. 21. All that is then necessary is to put the upper part 134 of the syringe body 102 into place. As in the syringe shown in FIG. 17, the cover plate 136 of this upper part 134 is provided with recesses for the passage of the support surfaces 116 of the shaft 112.

Figure 23:
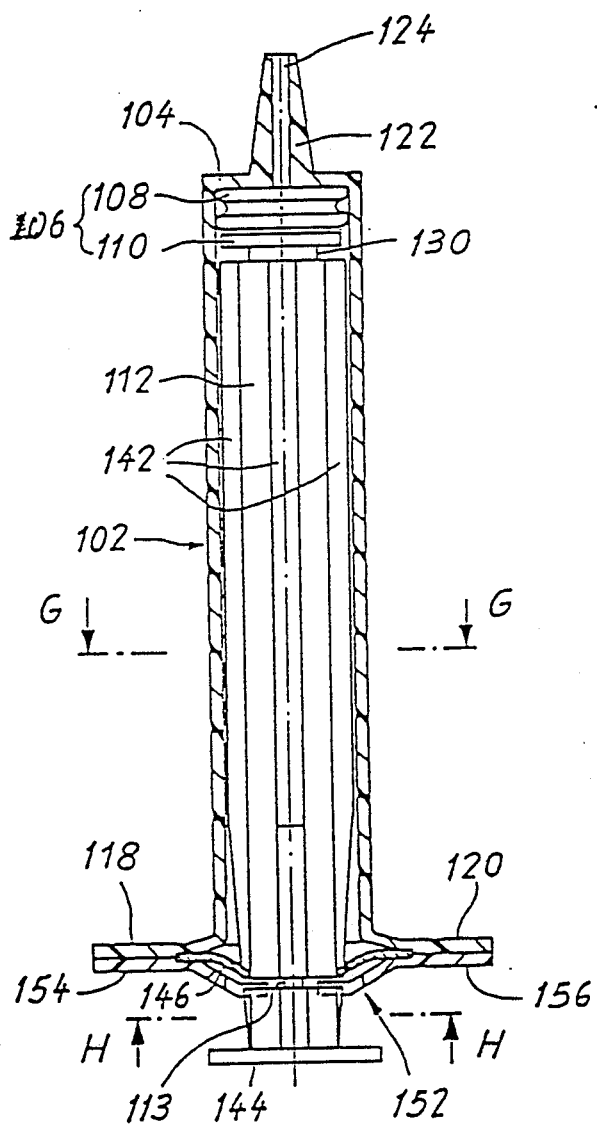
FIG. 23 is a longitudinal section illustrating another embodiment of the syringe element according to the invention.
Figure 24:
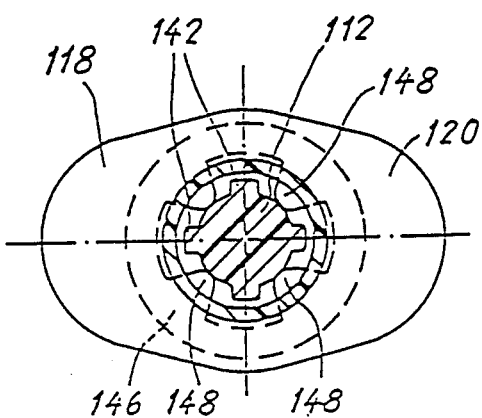
FIG. 24 is a transverse section along the axis GG of FIG. 23.
Figure 25:
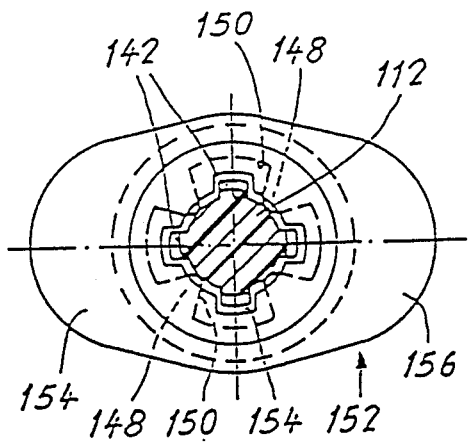
FIG. 25 is a transverse section along the axis HH of FIG. 23.

A syringe element according to another embodiment of the invention is shown in longitudinal section in FIG. 23 and in transverse sections about the axes GG and HH respectively in FIGS. 24 and 25.

This syringe element has a syringe body 102 of conventional shape comprising a cylindrical body terminated at a lower extremity by a base 104 and expanding at the upper extremity to give rise to two support surfaces 118 and 120. The base 104 has a cone 122, pierced by a channel 124, designed to receive a hollow needle. The shaft 112 is composed of a solid cylinder provided with guide wings 142. These make it possible to better guide the movement of the shaft in the syringe body 102. These guide wings can be withdrawn since the shaft is already guided in its displacement by the flexible plate of the invention. The shaft 112 is terminated at one extremity by a piston 106, comprising a resilient element 108 fixed to a rigid support 110 and to the other extremity by a support surface 144.

This syringe element is provided with a flexible plate 146 fixed to the syringe body 102 and resting resiliently against the shaft 112. This also comprises a groove 130 in the part of the shaft 112 situated near the piston 106. The plate here has the shape of a washer provided with a plurality of fingers 148 resting against the shaft 112. This washer also has recesses 150 permitting the passage of the guide wings 142 of the shaft 112.

The washer 146 is placed on the support surfaces 118 and 120 constituting the upper part of the syringe body 102. A piece 152 is then fitted to close the upper extremity of the syringe and prevent any access to the washer 146. This piece 152 has recesses 154 for the passage of the guide wings 142 of the shaft 112. It also has support surfaces 154, 156 to simplify handling of the shaft 112.

The syringe element of the invention shown in FIGS. 23 to 25 can thus be produced simply and at low cost on the basis of a conventional syringe through addition of a washer 146 and a piece 152 and the realization in the shaft 112 of a groove 130 and a zone 113 of weak resistance.

As regards the undetachable needle of the invention, it should be noted that there are two reasons why drug addicts have to be able to detach the needle from the syringe barrel. On the one hand it is not easy to carry in one's pocket a syringe the needle of which is mounted on the syringe barrel and, on the other hand, the liquid is generally drawn up into the syringe barrel from a shallow recipient—typically a spoon—which is not possible in practice if the drawing up is effected directly into the syringe barrel, the needle only being put in place after the liquid is draw up.

There is presumably little risk that a syringe, the needle of which cannot be dismantled once it is in position, would be retained by a drug addict or exchanged between drug addicts. The result is a significant reduction in the likelihood of virus transmission between drug addicts.

In a more general context, the syringe of the invention is also of interest in that, when it is also provided with means which only permit a single drawing up-injection movement of the piston of the syringe and which block or pierce the piston after this movement. The syringe is then totally unusable after its first use. This removes the risk of even involuntary or inadvertent reuse of any part whatsoever of an already used syringe. A security aspect of this nature is particularly important in a medical practice or in a hospital environment.

A further object of the present invention is therefore a syringe provided with fixing means which prevent detachment of the needle after this has been put in position, and also provided with means which destroy the seal between the needle and the syringe barrel when the fixing means are removed.

More specifically, this further object of the invention is to provide a syringe comprising a syringe barrel having a lower extremity closed by a base and an open upper extremity, said base comprising a nozzle pierced by a channel; a shaft terminated by a piston sliding inside said syringe barrel; and a hollow needle comprising a base and a conduit, said base having a cavity to permit said base to fit in sealed manner onto said nozzle by linking said conduit to said syringe barrel by the intermediary of said channel, this syringe being characterized in that it comprises at least one fixing means, each fixing means being composed of a tongue on the outside face of the nozzle, each tongue comprising a cavity communicating with the channel, and an indentation on the inside face of the base, said fixing means being disposed to permit the attachment onto and prevent the detachment of the needle from the syringe barrel, this syringe also comprising means for linking each indentation to the outside of the syringe.

The characteristics and advantages of the invention are shown more clearly in the following description, given for purposes of illustration, but which are not limiting, with references to the enclosed drawings, in which:

FIG. 26 is a longitudinal section of a syringe according to the invention,

FIG. 27 is a longitudinal section showing in detailed manner the fixing of the needle to the syringe barrel of the syringe illustrated in FIG. 26

Figure 31:
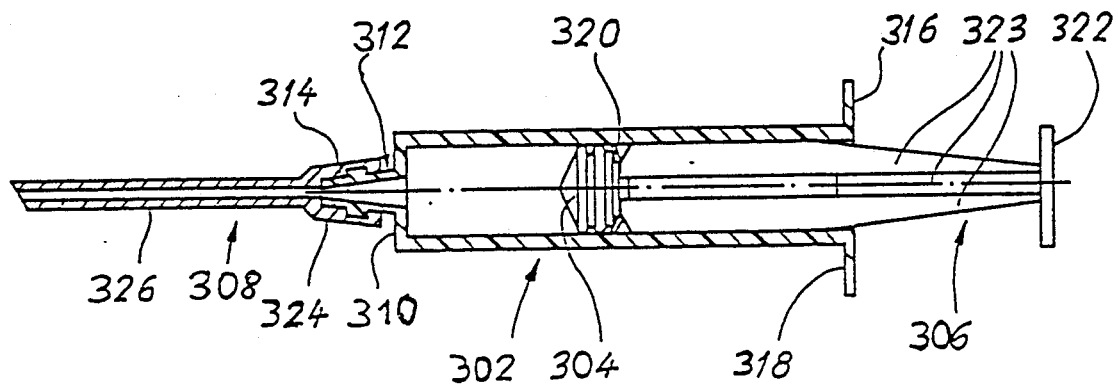
Figure 32:
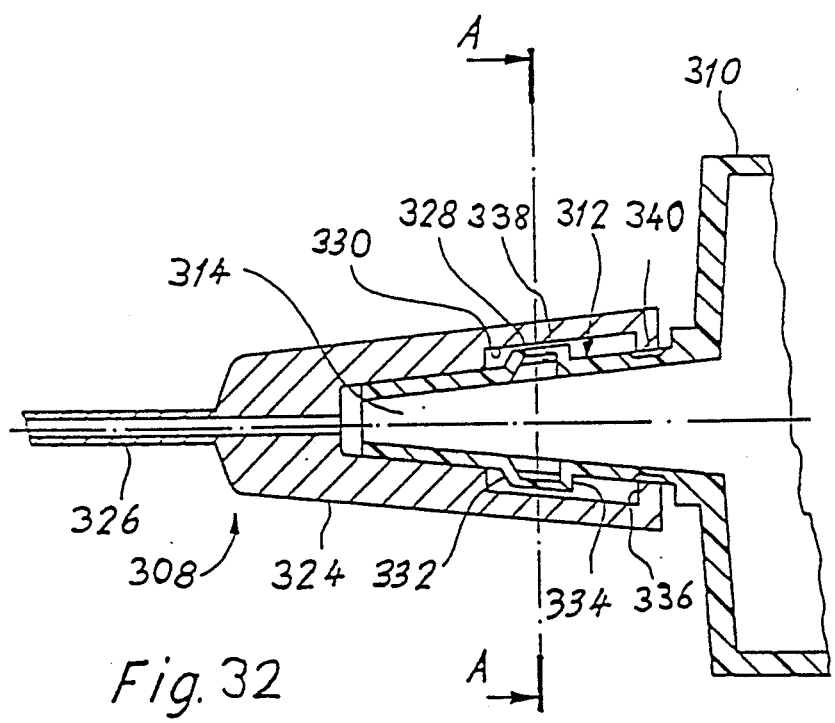
Figure 34:
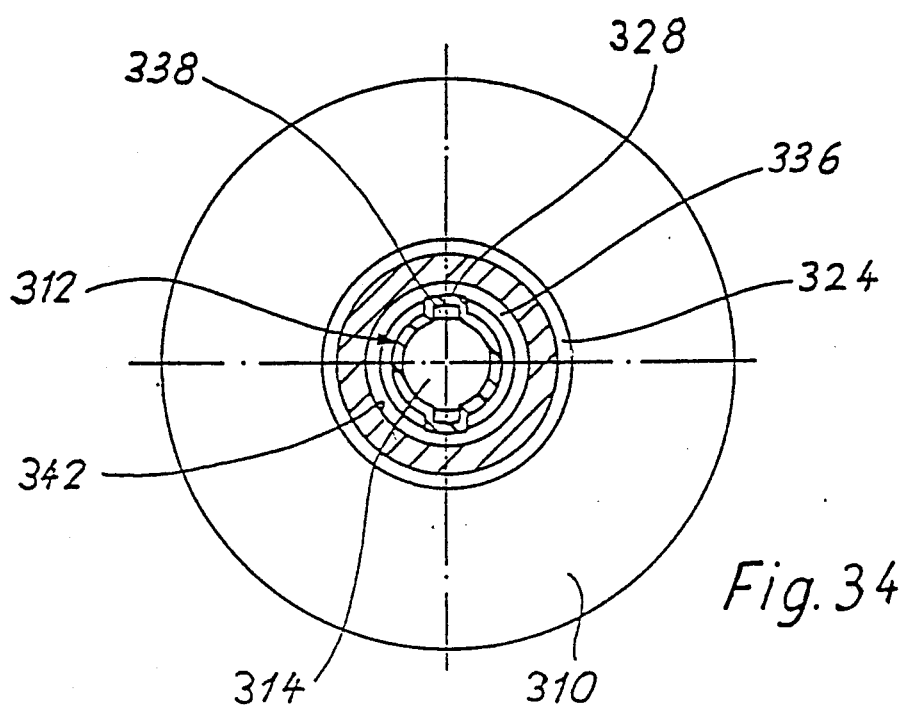
Figure 33:
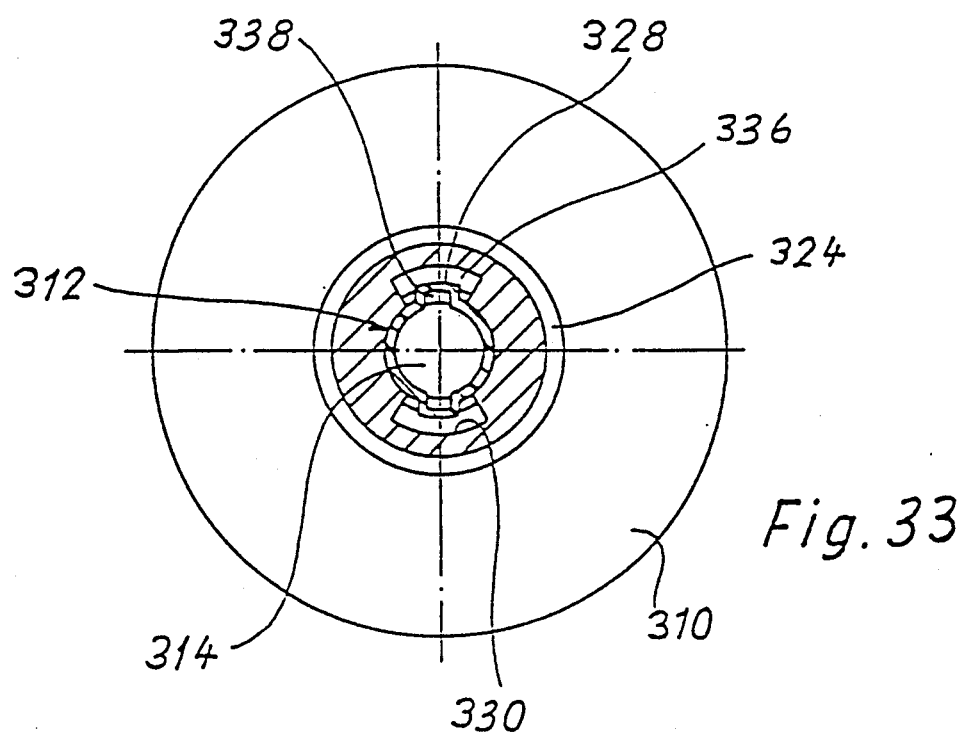
Figures 35, 36, 37:
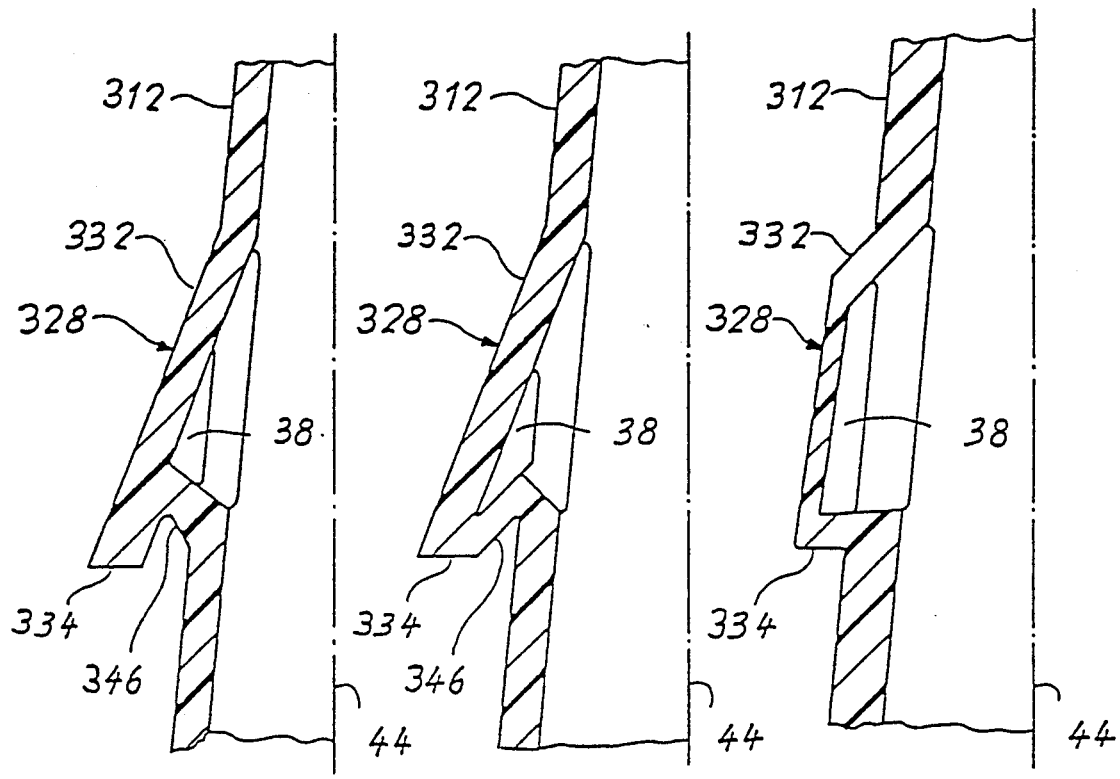
Figure 38:
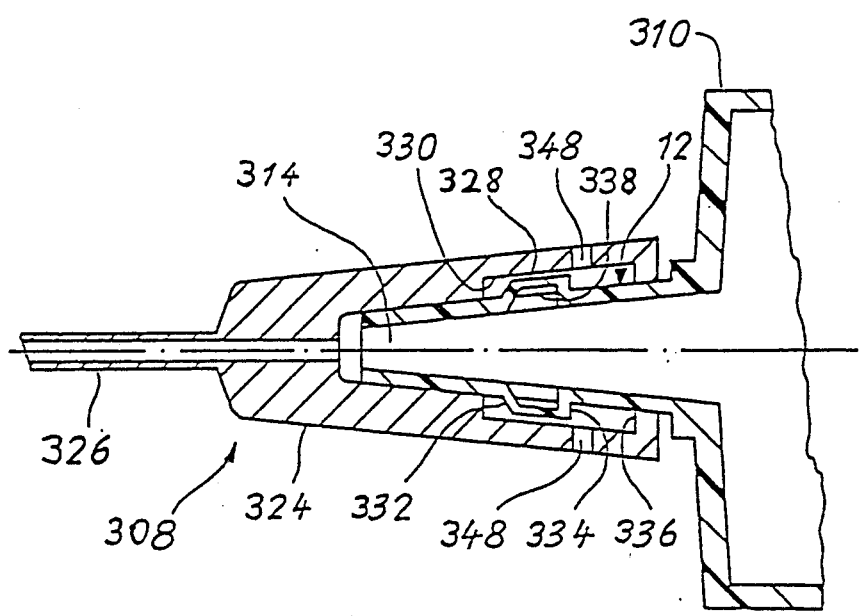

FIG. 28 is a transverse section along the axis AA of FIG. 27,

FIG. 29 is a transverse section illustrating an embodiment of the indentations effected in the base of the needle, FIGS. 30, 31 and 32 illustrate different embodiments of the tongues and FIG. 33 is a longitudinal section similar to FIG. 27 but comprising different means for linking each indentation to the outside of the syringe.

There is shown in FIG. 26 a longitudinal section of a syringe according to the invention. This syringe is, for example, cylindrical, but it is evident that the invention is not bound to any particular shape of cross section of the syringe.

The syringe shown conventionally comprises a syringe barrel 302, a piston 304 sliding inside the syringe barrel, a shaft 306 for displacing the piston 304 and a hollow needle 308.

The syringe barrel 302 has an extremity, termed lower extremity, closed by a base 310 which is extended by a nozzle 312 pierced by a channel 314. The nozzle 312 has the shape of a truncated cone, but may also be cylindrical in shape. The other extremity, or upper extremity, of the syringe barrel 302 is provided with support surfaces 316, 318 which facilitate the injection procedure.

The shaft 306 is terminated at one extremity by a cover plate 320 on which is fixed the piston 304 and at another extremity by a support surface 322 used to facilitate displacement of the shaft. Guide wings 323 are also provided to guide the shaft as it slides inside the syringe barrel.

Finally, the needle 308 has a base 324 and a conduit 326. The base 324 has a truncated conical cavity which enables the needle 308 to be mounted in tight manner onto the nozzle 312 of the syringe barrel, whilst enabling the conduit 326 to communicate with the syringe barrel via the intermediary of the channel 314.

Finally, the syringe shown has, in accordance with the invention, fixing means each composed of a tongue and an indentation, and means to link each indentation to the outside of the syringe.

These means will be described with reference to FIG. 27 which shows in detailed manner the nozzle 312 of the syringe barrel 302 and the base 324 of the needle 308.

Each fixing means comprises a tongue 328 disposed on the outside face of the nozzle 312 and an indentation 330 bored in the inside face of the base 324 and constituting a bed for the tongue when the needle is mounted on the syringe barrel.

These fixing means are disposed in such a manner as to permit attachment of the needle, but not its detachment. For this purpose, each tongue 328 has a first extremity 332 which presents a face that is inclined with respect to the axis of the syringe of facilitate insertion of the syringe and a second extremity 334 which presents a face that is substantially perpendicular to the axis of the syringe and which cooperates with the face of an extremity 336 of the indentation to prevent dismantling of the needle.

In accordance with the invention, each tongue 328 is provided with a cavity 338 which communicates with the channel 314 of the nozzle. In addition, means such as the indentations 340 bored in the surface of the nozzle 312 are provided to link each indentation to the outside of the syringe.

The role of the cavities 338 and the indentations 340 is the following. The shape of the nozzle and the shape of the cavity of the base are chosen so that there is tightness between the needle and the syringe barrel when the needle is in place. If tongues are present, the needle cannot be dismantled. In this case the cavities 338 and the indentations 340 fulfill no function.

On the other hand, if the user of the syringe removes the fixing means in order to be able to attach and detach the needle at will, the cavities 338 and the indentations 340 destroy the tightness of the assembly, thus rendering the syringe unusable.

In fact, it is impossible to remove the fixing means by eliminating the extremity 336 of each indentation since the needle is generally made of steel. Removal of the fixing means therefore consists in eliminating the tongues, generally of plastic material, for example using a razor blade. However, this removal provides for communication between each indentation 330 and the channel 314 via a cavity 338. Since the indentations 330 are also linked to the outside of the syringe by recesses 340, the liquid contained in the syringe barrel is finally partially expelled during injection by the recesses 340. In addition, expulsion of the liquid creates a pressure on the base of the indentations which tends to separate the needle from the syringe barrel. The needle is therefore unusable.

FIG. 27 illustrates an embodiment of the constituent means of the invention. In this figure, the indentations 330 have a length considerably greater that the tongues 328. It is nevertheless clear that the indentations can have a length only slightly greater than that of the tongues.

FIGS. 28 and 29 illustrate two embodiments of the indentations. These figures show transverse sections along the axis AA of FIG. 29. The elements shown in FIGS. 33 and 29 and which are identical to those in FIG. 27 have the same references.

In FIG. 28 the indentations 330 have a width slightly greater than that of the tongues, whereas on FIG. 29 the indentations are constituted by a single neck 342.

The number and arrangement of the tongues and indentations can of course differ from those illustrated in FIGS. 28 and 29.

FIGS. 30 and 32 show different possible shapes for the tongues. In each figure the tongue 328 comprises a first extremity 332 inclined in such a manner as to facilitate insertion of the needle and a second extremity 334 having a face that is substantially perpendicular to the axis 344 of the syringe in such a manner as to prevent extraction of the needle.

The first extremity 332 is in contact with the outside surface of the nozzle 312 whereas the second extremity can, on the other hand, be separated therefrom by claws 346 (FIGS. 30 and 31). These claws 346 give greater resilience to the tongue 328 and thus favour insertion of the needle.

All the tongues 328 have, in conformity with the invention, a cavity 338 which forms a hole in the nozzle 312 when the tongue is removed.

In this case, each indentation 330 communicates with the channel 314 and the tightness disappears due to recesses 340 (FIG. 27) provided on the surface of the nozzle.

These recesses can be replaced by holes 348 effected in the base 324 of the needle, as has been shown in FIG. 33. In this figure, elements identical to those of FIG. 32 carry the same references. The holes 348 link the indentations 330 on the inside face of the base 324 directly to the outside face of this base 324.

Industrial Application

The syringe elements, syringes and needles of the invention prevent the spread of disease, especially retroviral diseases such as hepatitis and AIDS. This is accomplished by the syringes self-destructing on attempted re-use.

I claim:

1. In a non-reusable syringe element having a syringe body with a lower barrel portion of uniform diameter inner walls and closed by a base pierced with a channel, an opened upper barrel portion, a piston disposed in and tightly slidable in the lower barrel portion, a shaft disposed in said barrel portions with a shaft lower extremity attached to said piston and a shaft upper extremity projecting beyond said upper barrel portion, wherein said piston is displaceable by said shaft along said lower barrel portion, and a friction means for imposing a friction such that a weak frictional force results when the piston is displaced in said lower barrel portion in one direction and a strong frictional force results when the piston is displaced in said lower barrel portion in the other direction, the improvement wherein the friction means comprises:

(1) at least one flexible and resilient plate operably disposed on said shaft with outward peripheral edges of said plate being in contact with the inner walls of said lower barrel portion, said plate having on each side thereof a collar which has a configuration such that said plate is positioned and held between said collars but wherein the peripheral edges of said plate are free to move from a generally concave configuration to a convex configuration;

(2) a portion of said plate disposed at least at said peripheral edges thereof such that when the plate is disposed within said lower barrel portion at least the peripheral edges of the plate can assume said generally concave or convex configuration wherein the piston may be displaced inwardly or outwardly in said lower barrel portion and such that said weak frictional force is generated when the piston is displaced in said lower barrel portion in a direction tending to increase the curvature of the plate and strong frictional force is generated when the piston is displaced in said lower barrel portion in a direction tending to decrease the curvature of the plate; and (3) a portion of weak traction resistance on said shaft such that the traction force on said shaft necessary to separate the shaft at said portion of weak traction resistance is between the said weak frictional force and the said strong frictional force.

2. A syringe element according to claim 1, characterized in that said friction means is a flexibly resilient washer having a hole and said shaft comprises a part crossing said hole and two collars wider than said hole between which the washer is held.

3. A syringe element according to claim 2 characterized in that said part of the shaft has a section weaker than the rest of the shaft.

4. A syringe element according to claim 2 characterized in that said part of the shaft forms said zone of weak resistance.

5. A syringe element according to claim 1 in which, before use, the product to be injected is already contained in the syringe body characterized in that the plates forming the friction means are elastically curved with their concavity turned towards the upper extremity of the syringe body.

6. A syringe element according to claim 1 in which, before use, the piston is near the base of the syringe body and the plates forming the friction means are resiliently curved with their concavity turned towards the piston, characterized in that the inner face of said syringe body comprises a groove disposed to receive the plates forming the friction means at the end of the drawing up phase.

7. A syringe element according to claim 1 characterized in that the friction means is placed on the shaft at a distance from the piston at least equal to the length of the stroke of the piston.

8. A syringe element according to claim 1 characterized in that it comprises means (72, 76) preventing the shaft (42) from being completely withdrawn from the syringe body (32).

9. A non-reusable syringe characterized in that it comprises a syringe element according to claim 1 and a hollow needle adaptable in tight manner to the base of the syringe body.

* * * * *